(12) United States Patent
Claussen et al.

(10) Patent No.: US 12,742,770 B2
(45) Date of Patent: Sep. 22, 2026

(54) MENSTRUAL FLUID SIMULANT

(71) Applicant: The Procter & Gamble Company, Cincinnati, OH (US)

(72) Inventors: Jan Claussen, Wiesbaden (DE); Behzad Mohebbi, Schwalbach am Taunus (DE); Christian Neu, Hesse (DE); Alexandra Wolf, Hessen (DE); Raffaele Graziano, St. Gilles (BE); Laura Bordón Viloria, Madrid (ES); Dennis Winston Woertge, Hessen (DE); Pieter Jan Maria Saveyn, Destelbergen (BE); Michelle Natasha Adams-Hughes, Fairfield, OH (US); Christopher Philip Bewick-Sonntag, Cincinnati, OH (US); Marc Johan Declercq, Strombeek-Bever (BE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 270 days.

(21) Appl. No.: 18/500,179

(22) Filed: Nov. 2, 2023

(65) Prior Publication Data

US 2024/0151706 A1 May 9, 2024

Related U.S. Application Data

(60) Provisional application No. 63/422,144, filed on Nov. 3, 2022.

(51) Int. Cl.
*G01N 33/36* (2006.01)
*G01N 33/00* (2006.01)

(52) U.S. Cl.
CPC ......... *G01N 33/36* (2013.01); *G01N 33/0078* (2024.05)

(58) Field of Classification Search
None
See application file for complete search history.

(56) References Cited

FOREIGN PATENT DOCUMENTS

CN 106908367 A 6/2017

OTHER PUBLICATIONS

Extended European Search Report and Written Opinion for 23207433.6 dated Mar. 20, 2024, 8 pages.

*Primary Examiner* — Daniel S Larkin
(74) *Attorney, Agent, or Firm* — Sarah M. DeCristofaro

(57) ABSTRACT

The present disclosure relates to menstrual fluid simulant compositions that mimic the properties of real menstrual fluid, where the menstrual fluid simulant compositions comprise vesicle dispersions of quaternary ammonium compounds and linear polymers. The present disclosure also relates to related methods and uses.

20 Claims, 3 Drawing Sheets

MENSTRUAL FLUID SIMULANT

FIELD OF THE INVENTION

The present disclosure relates to menstrual fluid simulant compositions that mimic the properties of real menstrual fluid, where the menstrual fluid simulant compositions comprise vesicle dispersions of quaternary ammonium compounds and linear polymers. The present disclosure also relates to related methods and uses.

BACKGROUND OF THE INVENTION

Personal care absorbent products abound in the market place. Such products are used by persons of all ages and include diapers, training pants, adult incontinence articles and feminine hygiene products, such as tampons and sanitary napkins. Personal care absorbent products are often subjected to efficacy testing during the product development phase as well as to substantiate advertising claims directed to the commercialized product.

Efficacy testing may be completed in vivo and/or in vitro. In vivo tests may require panelists to wear a product for a finite time and then return the used product for data collection and evaluation. In vivo testing can be costly and time-consuming. Moreover, in vivo testing exposes the data collector to the potential risk of contact with bodily fluids and associated pathogens. In vitro testing may also offer a higher degree of experimental control and precision than in vivo testing. For these reasons, in vivo test procedures and artificial body exudates have been developed for in vitro testing. For instance, the developers of feminine hygiene products have liquid substitutes for menstrual fluid that are used in laboratory testing and efficacy demonstrations.

Menstrual fluid is a complex biological fluid that may contain blood, vaginal secretions, endometrial cells of the uterine wall, sloughed vaginal epithelial cells, and/or endogenous vaginal microbes. As such, menstrual fluid has a broad range of fluid properties, such as viscosity, breakup time, and surface tension (which are also quite different from the properties of blood). Importantly, these properties affect the interaction of menstrual fluid with the porous surfaces and absorbent materials that form feminine hygiene products, as demonstrated in FIG. 1. Also, the consistency and fluid properties of real menstrual fluid are highly variable from woman to woman and may even vary with regard to an individual woman over the course of her menstrual period. In order for in vitro testing of absorbent feminine hygiene products to provide data that correlate to consumer perceptible differences, a menstrual fluid simulant that closely emulates the wide-ranging physical properties of real menstrual fluid is desired.

Existing artificial menstrual fluid simulants do not emulate the properties of real menstrual fluid. For example, some artificial simulants, such as saline and Paper Industrial Fluid (PIF), are liquid solutions with all of the solids present dissolved therein. More specifically, Paper Industrial Fluid (PIF) is a Newtonian fluid that may be prepared by dissolving the following components in 1 liter of deionized water in the amounts indicated: glycerol (80 g/L), NaCl (10 g/L), $NaHCO_3$ (4 g/L), sodium carboxymethylcellulose (15 g/L) (e.g., C5678, available from Sigma-Aldrich). Such artificial simulants that lack insoluble solids tend to be absorbed more readily by feminine hygiene products than real menstrual fluid, which is a multiphase suspension of particulate matter in combination with glycoproteins in an aqueous liquid.

Other artificial simulants contain blood and, optionally, mucus, both derived from animals, such as a sheep and pigs. However, the properties of such blood-based (with or without mucus) simulants are very different from the properties of real menstrual fluid, because the properties of blood are very different from the properties of menstrual fluid, as noted above. Furthermore, artificial menstrual fluid simulants that contain animal-derived materials have other disadvantages. Artificial menstrual fluids that contain animal-derived materials typically have a limited shelf life and may require in vitro testing to take place in special laboratories, which are certified for handling animal-derived materials. Also, the use of artificial menstrual fluids that contain animal-derived materials may also be perceived by some consumers as unsustainable.

More importantly, conventional artificial menstrual fluid simulants are not tunable, meaning that the properties of conventional artificial menstrual fluid simulants cannot be tuned or adjusted to reflect the wide-ranging properties exhibited by real menstrual fluid and experienced by consumers (for example, at different points in a consumer's cycle, after sitting or lying down), in order to describe the interaction between real menstrual fluid and an absorbent feminine hygiene product and/or to provide more precise and correlative in vitro lab tests. Thus, there is a need for an artificial menstrual fluid, particularly a non-animal-based artificial menstrual fluid, that emulates the wide-ranging properties of real menstrual fluid.

SUMMARY OF THE INVENTION

A menstrual fluid simulant composition comprising:

a. from about 1 to about 60% by weight of the simulant composition of a vesicle dispersion of a quaternary ammonium compound of Formula (I) or Formula (II), preferably Formula (I):

$$\{R_{4-m}—N^{+}—[Z—Y—R^{1}]_{m}\}X^{-} \quad (I)$$

$$[R_{4-m}—N^{+}—R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—CH$(CH_3)$— or CH—$(CH_3)$—$CH_2$—; each Y comprises —O—(O)C—, —C(O)—O—, —NR—C(O)—, or —C(O)—NR—; each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b. from about 0.1% to about 3% by weight of the simulant composition of a linear, nonionic polymer having a viscosity average molecular weight ($M_V$) greater than or equal to 100 kDA and less than 25,000 kDA;

c. from about 0.05% to about 0.9% by weight of the simulant composition of an inorganic salt;

d. from about 0.1% to about 2% by weight of the simulant composition of a dye; and e. water, preferably deionized water;

where the menstrual fluid simulant composition has a viscosity that is shear-dependent and ranges from about 10 mPas to about 140 mPas, at 21° C. and a shear rate of 10 $s^{-1}$.

A menstrual fluid simulant composition comprising:

a. from about 1 to about 60% by weight of the simulant composition of a vesicle dispersion of a quaternary ammonium compound of Formula (I) or Formula (II), preferably Formula (I):

$$\{R_{4-m}—N^{+}—[Z—Y—R^{1}]m\}X^{-} \quad (I)$$

$$[R_{4-m}—N^{+}—R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—CH $(CH_3)$— or CH—$(CH_3)$—$CH_2$—; each Y comprises —O—(O)C—, —C(O)—O—, —NR—C(O)—, or —C(O)—NR—; each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b. from about 0.1% to about 3% by weight of the simulant composition of a linear, nonionic polymer having a viscosity average molecular weight ($M_V$) greater than or equal to 100 kDA;

c. from about 0.05% to about 0.9% by weight of the simulant composition of an inorganic salt;

d. from about 0.1% to about 2% by weight of the simulant composition of a dye; and e. water, preferably deionized water;

where the menstrual fluid simulant composition has a filament breakup time of about 100 to about 3000 ms, preferably between about 200 ms and about 1500 ms, more preferably between about 300 ms and 800 ms, measured using the Capillary Breakup Extensional Rheometry (CaBER) described herein.

A menstrual fluid simulant composition comprising:

a. from about 1% to about 60% by weight of the simulant composition of a vesicle dispersion of a quaternary ammonium compound of Formula (I) or Formula (II), preferably Formula (I):

$$\{R_{4-m}—N^{+}—[Z—Y—R^{1}]m\}X^{-} \quad (I)$$

$$[R_{4-m}—N^{+}—R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—CH $(CH_3)$— or CH—$(CH_3)$—$CH_2$—; each Y comprises —O—(O)C—, —C(O)—O—, —NR—C(O)—, or —C(O)—NR—; each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b. from about 0.1% to about 3% by weight of the simulant composition of a linear, nonionic polymer having a viscosity average molecular weights ($M_V$) greater than or equal to 100 kDA;

c. from about 0.05% to about 0.9% by weight of the simulant composition of an inorganic salt;

d. from about 0.1% to about 2% by weight of the simulant composition of a dye; and e. water, preferably deionized water;

where the menstrual fluid simulant composition has a surface tension that ranges from about 35 mN/m to about 70 mN/m.

A menstrual fluid simulant composition, where the menstrual fluid simulant composition has a filament breakup time of about 100 to about 3000 ms, preferably between about 200 ms and about 1500 ms, more preferably between about 300 ms and 800 ms, measured using the Capillary Breakup Extensional Rheometry (CaBER) described herein, a viscosity that is shear-dependent and ranges from about 10 mPas to about 140 mPas, at 21° C. and a shear rate of 10 s-1, a surface tension that ranges from about 35 mN/m to about 70 mN/m, or a combination thereof.

A method of making a menstrual fluid simulant composition comprising the steps of:

a. dissolving a dye and an inorganic salt in water, preferably deionized water, to form a first solution and mixing the first solution;

b. adding a linear polymer having a molecular weight greater than or equal to 100 kDA to the first solution to form a second solution and mixing the second solution;

c. adding and optionally mixing a quaternary ammonium compound of Formula (I) or Formula (II), preferably Formula (I), to the second solution to form the menstrual fluid simulant composition:

$$\{R_{4-m}—N^{+}—[Z—Y—R^{1}]m\}X^{-} \quad (I)$$

$$[R_{4-m}—N^{+}—R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—CH $(CH_3)$— or CH—$(CH_3)$—$CH_2$—; each Y comprises —O—(O)C—, —C(O)—O—, —NR—C(O)—, or —C(O)—NR—; each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate.

DETAILED DESCRIPTION OF THE INVENTION

Figure 1:
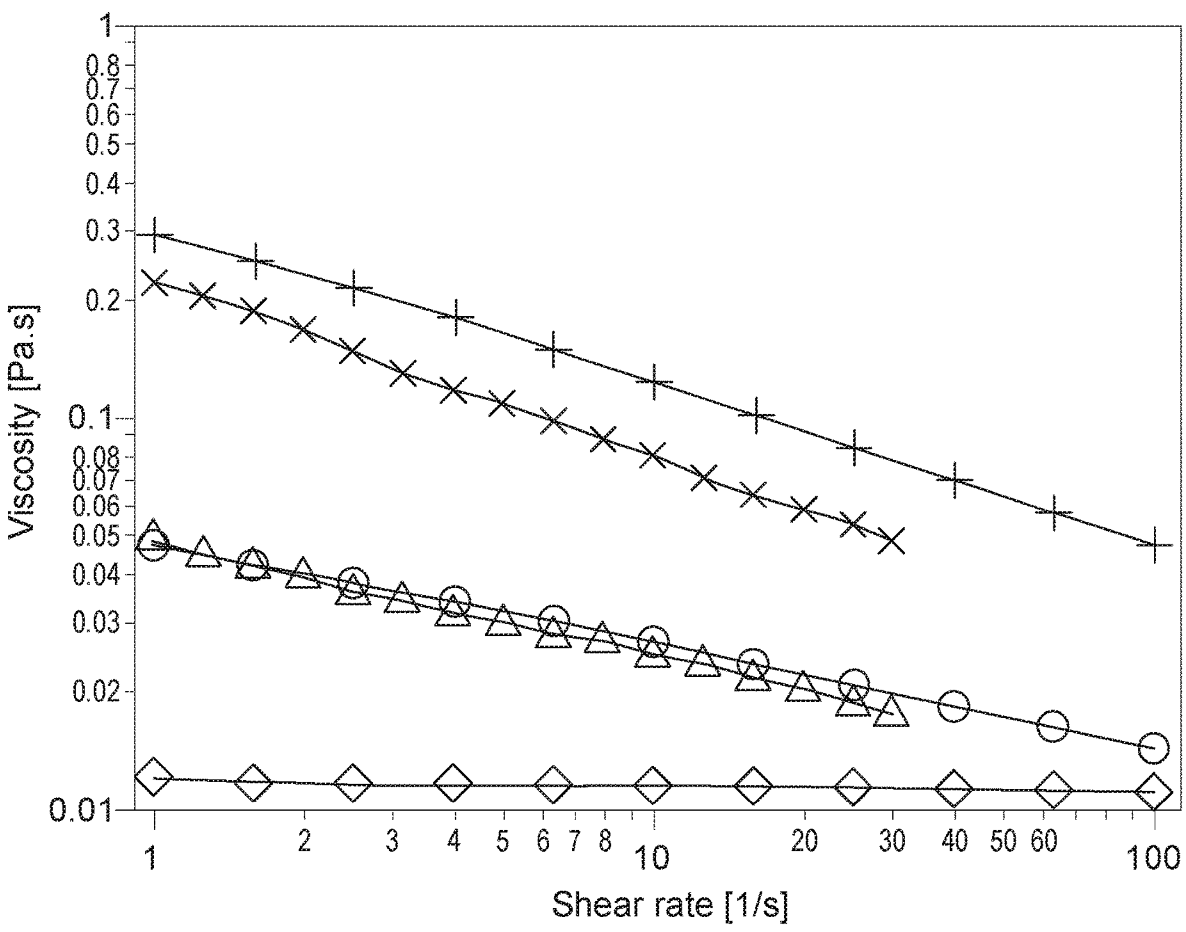
FIG. 1 is a graphic representation of viscosity as a function of shear rate for the menstrual fluid simulant example compositions 1 and 2, Paper Industrial Fluid (PIF), and two samples (high and low) of real menses.

Surprisingly, it has been found that an artificial menstrual fluid that mimics the properties of real menstrual fluid, such as viscosity and breakup time, can be achieved by combining a vesicle dispersion and a linear polymer. Moreover, an artificial menstrual fluid containing a combination of a vesicle dispersion and a linear polymer can be produced without the use of animal-based materials. A non-animal-based artificial menstrual fluid may be preferred over existing animal-based artificial menstrual fluids, due to its increased shelf life stability and the ability to test with the fluid outside of biohazard certified laboratories. Altogether, the artificial menstrual fluid disclosed herein may enable easier, more cost-effective in vitro testing of feminine hygiene products and deliver more reproducible results. Also, the properties of the artificial menstrual fluids disclosed herein can be tuned or adjusted to reflect the wide-ranging properties exhibited by real menstrual fluid and experienced by consumers, in order to explore the interaction of real menstrual fluid properties using the artificial menstrual fluids in the context of in vitro fluid handling product testing.

As used herein, the term "absorbent article" means a layered product including an absorbent core and configured to be worn externally about the lower torso and/or upper crotch region of a human being, and configured to contain and/or absorb bodily exudates which may include urine, menstrual fluid or feces. Examples of absorbent articles include feminine hygiene pads (also known as catamenial pads or sanitary napkins), male incontinence guards, disposable incontinence pads, absorbent underwear (configured for, e.g., managing incontinence) and diapers.

As used herein, "menstrual fluid" or "menses" may include uterine tissues, blood, extracellular fluids, mucus, secretions, glandular tissue of the endometrium, and/or any other biological materials discharged from the female reproductive tract. Likewise, "menstruation" can refer to any discharge of blood/menstrual fluid from the female reproductive tract at any time and during any phase of the menstrual cycle. Blood may include cells (e.g., erythrocytes, leukocytes, thrombocytes, etc.), water, serum, plasma, cholesterol, triglycerides, clotting factors, glucose, amino acids, lipids, fatty acids, lipoproteins, serum albumin, sodium chloride, urea, uric acid, lactic acid, vitamins, minerals, hormones, antibodies, plasma proteins, fibrin, fibrinogen, carbohydrates, iron, oxygen, carbon dioxide, bicarbonate ions, and/or nitrogen.

As used herein, a "liquid component of menstrual fluid" can include serum, plasma, extracellular fluids, liquid secretions, and/or any other liquid component of menstrual fluid in any combination. As used herein, "menstrual fluid particles" can include any solid or semi-solid component of menstrual fluid, such as tissue, mucous, mammalian cells (e.g., erythrocytes, leukocytes, etc.), and non-mammalian cells (e.g., protozoa, bacteria, yeast, fungi). "Tissue," as used herein, means a group (i.e. two or more) of mammalian cells physically coupled together. Examples of tissue include, but are not limited to, endometrial tissue, glandular tissue, and coagulated blood components (e.g., cells embedded within a fibrin matrix).

As used herein, the term "non-animal-based" means a composition that does not comprise animal-derived materials or components, such as animal-derived mucus, animal-derived whole blood, animal-derived reconstituted blood, animal-derived blood constituents, such as red blood cells or plasma, or tallow quaternary ammonium compounds. Whole blood is blood from which no constituent, such as plasma, has been removed. Reconstituted blood comprises red blood cells that are separated from the other components found in whole blood, which is then reconstituted with plasma, aqueous buffer, or combinations thereof.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

Unless otherwise noted, all component or composition levels are in reference to the active portion of that component or composition, and are exclusive of impurities, for example, residual solvents or by-products, which may be present in commercially available sources of such components or compositions. All percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Menstrual Fluid Simulant Compositions

The present disclosure relates to menstrual fluid simulant compositions. More specifically, the present disclosure relates to menstrual fluid simulant compositions that comprise a vesicle dispersion and a linear polymer. The combination of a vesicle dispersion and a linear polymer provides a stable menstrual fluid simulant composition that mimics the properties of real menstrual fluid, such as, viscosity and breakup time.

The menstrual fluid simulant compositions of the present disclosure may have a viscosity that is shear-dependent and ranges from about 10 mPa·s to about 140 mPa·s, or from about 20 mPa·s to about 130 mPa·s, or from about 30 mPa·s to about 120 mPa·s, or from about 40 mPa·s to about 110 mPa·s, or from about 50 mPa·s to about 100 mPa·s, at 21° C. and a shear rate of 10 $s^{-1}$. The viscosity of the menstrual fluid simulant compositions may decrease as shear rate increases.

The menstrual fluid simulant compositions of the present disclosure may have a filament breakup time of about 100 to about 1500 ms, preferably between about 200 ms and about 1000 ms, more preferably between about 300 ms and 800 ms, measured using the Capillary Breakup Extensional Rheometry (CaBER) described herein.

The menstrual fluid simulant compositions of the present disclosure may have a surface tension that ranges from about 35 mN/m to about 70 mN/m, or about 40 mN/m to about 65 mN/m, or about 45 mN/m to about 60 mN/m.

Preferably, the menstrual fluid simulant compositions are non-animal-based.

Vesicle Dispersion

The menstrual fluid simulant compositions disclosed herein comprise vesicle dispersions, particularly vesicle dispersions of quaternary ammonium compounds. The menstrual fluid simulant compositions may comprise about 1 to about 60%, or about 10% to about 60%, or about 20% to about 50%, by weight of the simulant compositions of the vesicle dispersion(s). It is believed that vesicle dispersions of quaternary ammonium compounds mimic the red blood cells found in real menstrual fluid. The vesicle dispersions of quaternary ammonium compounds may also help to build viscosity in the menstrual fluid simulant compositions. The vesicle dispersion may comprise, in addition to the quaternary ammonium compound, a pH-adjusting agent. The vesicle dispersion may contain spherical vesicles, non-spherical vesicles, non-spherical lipid bilayer structures, or a combination thereof. The vesicle dispersion may, for example, contain a fraction of spherical vesicles and a fraction of non-spherical lipid bilayer structures. The vesicle dispersion is generally acidic to improve the hydrolytic stability of the quaternary ammonium compound and the pH may be from about 2.0 to about 6.0, preferably from about 2.0 to about 4.5, more preferably from about 2.0 to about 3.5. Improved hydrolytic stability of the vesicle dispersion may contribute to improving the shelf life of the menstrual fluid simulant containing the vesicle dispersion. Non-limiting examples of pH-adjusting agents include formic acid and hydrochloric acid (HCl).

The vesicle dispersion may be selected from commercially available fabric softeners that are based on aqueous dispersions of water-insoluble quaternary ammonium esters, preferably fabric softeners that are free of dyes and perfumes, such as Ultra Downy® Free & Gentle™. Vesicle dispersions, particularly vesicle dispersions based on commercially available fabric softeners, may optionally comprise additional components, such as a silicone antifoam, a chelant, and a solvent, such as isopropanol or other low molecular weight alcohols.

The vesicle dispersion may have a mean particle size diameter ranging from about 1 μm to about 10 μm. The particle size distribution of the vesicle dispersion may be measured using the HORIBA™ Light Scattering Technique. The term "HORIBA™ Light Scattering Technique" refers to a technique where particle-size distribution (as an average particle diameter size) is determined using a HORIBA™ LA-950 Laser Scattering Particle Size Distribution Analyzer equipped with a flow cell. The vesicle dispersion is added droplet wise, with sufficient waiting times for proper dispersion, to approximately 150 mL of deionized water, which contains the same concentration of HCl as the vesicle dispersion, in the sampling chamber (so that the transmission intensity is 80±1%). The sample is circulated and analyzed, once proper dispersion is accomplished. Thereafter, the particle size distribution is measured using Horiba LA950 Measurement Program—Horiba NextGen Project LA-950 for Windows P2000074001R 7.20, release date: 27 Apr. 2012 using the volume distribution base and a Kernel file with refractive index of 1.47 and virtual index 0.01.

Quaternary Ammonium Compounds

The vesicle dispersions disclosed herein comprise from about 0.1% to about 10%, or from about 1% to about 9%, or from about 2% to about 8%, by weight of the vesicle dispersions, of quaternary ammonium compounds, described in more detail below. The vesicle dispersions may comprise from about 2% to about 7%, or from about 3% to about 6%, of the quaternary ammonium compounds.

The quaternary ammonium compounds may be derived from a fatty acid feedstock. The fatty acid feedstock comprises fatty acids. The fatty acids may be derived from plants. Suitable sources of plant-derived fatty acids may include vegetable oils, such as canola oil, safflower oil, peanut oil, sunflower oil, sesame seed oil, rapeseed oil, cottonseed oil, corn oil, soybean oil, tall oil, rice bran oil, palm oil, palm kernel oil, coconut oil, other tropical palm oils, linseed oil, tung oil, and the like. Thus, the fatty acid feedstock may comprise fatty acids derived from plants, preferably derived from vegetable oils, more preferably derived from canola oil, safflower oil, peanut oil, sunflower oil, sesame seed oil, rapeseed oil, cottonseed oil, corn oil, soybean oil, tall oil, rice bran oil, palm oil, palm kernel oil, coconut oil, other tropical palm oils, linseed oil, tung oil, or mixtures thereof.

The fatty acid feedstock may be partially hydrogenated, as such processes can provide the desired amount of trans fatty acids. A partially hydrogenated fatty acid feedstock may be obtained by partially hydrogenating the fatty acids themselves, partially hydrogenating the oil from which the fatty acids are derived, or both. Also, a partially hydrogenated fatty acid feedstock may be obtained by blending a fully hydrogenated feedstock with a non-hydrogenated feedstock. Fatty acids that are derived from cottonseed, rapeseed, sunflower seed, or soybean may have a favorable trans-unsaturation content upon partial hydrogenation. The fatty acid may comprise, at least in part, partially hydrogenated fatty acids derived from cotton seed oil, as such materials may have favorable distributions of fatty acid types and trans-unsaturated bonds.

The fatty acids may include an alkyl portion containing, on average by weight, from about 13 to about 22 carbon atoms, or from about 14 to about 20 carbon atoms, preferably from about 16 to about 18 carbon atoms, where the carbon count includes the carbon of the carboxyl group. The population of fatty acids may be present in a distribution of alkyl chains sizes. A particular fatty acid may be characterized by the number of carbons in its alkyl portion. For example, a fatty acid having sixteen carbons in the alkyl portion may be called a "C16 fatty acid." Likewise, a fatty acid having eighteen carbons in the alkyl portion may be called a "C18 fatty acid." The fatty acid feedstock may comprise from about 50% to about 85%, preferably from about 60% to about 80%, more preferably from about 70% to about 80%, by weight of the fatty acid feedstock, of C18 fatty acids.

The alkyl quaternary ammonium compounds may comprise compounds formed from fatty acids that are unsaturated, meaning that the fatty acids comprise at least one double bond in the alkyl portion. The fatty acids may be monounsaturated (one double bond), or they may be diunsaturated (or double-unsaturated; two double bonds). The fatty acids may comprise unsaturated C18 chains, which may include a single double bond ("C18:1") or may be double unsaturated ("C18:2"). (For reference, a fatty acid with a saturated C18 chain may be referred to as "C18:0".) The double bond(s) of an unsaturated fatty acid may be in the "cis" or in the "trans" conformation.

The fatty acid feedstock may be characterized by an iodine value, which relates to the amount of unsaturated fatty acids in the feedstock. The fatty acid feedstock may be characterized by an iodine value of from about 1 to about 60, or from about 5 to about 50, or from about 10 to about 35, or from about 15 to about 30. It may be desirable that the fatty acid feedstock include some trans-unsaturated fatty acids in order to build viscosity in the final menstrual fluid simulant composition. Additionally, it is believed that feedstocks having relatively high levels of unsaturated fatty acid chains (for example, as indicated by a relatively high iodine value) are less likely to build viscosity as well as feedstocks characterized by lower levels and/or lower iodine values. Iodine value is determined according to the methods described in US Patent Publication No. 20220154106A1.

Suitable quaternary ammonium compounds (also referred to herein as "quats") include, but are not limited to, ester quats, amide quats, imidazoline quats, alkyl quats, amidoester quats, or combinations thereof.

Suitable alkyl quaternary ammonium compounds may be derived from alkanolamines, for example, C1-C4 alkanolamines, preferably C2 alkanolamines (e.g., ethanolamines). The quaternary ammonium compounds may be derived from monoalkanolamines, dialkanolamines, trialkanolamines, or mixtures thereof, preferably monoethanolamines, diethanolamines, di-isopropanolamines, triethanolamines, or mixtures thereof. The quaternary ammonium compounds may be derived from diethanolamines. The quaternary ammonium compounds may be derived from di-isopropanolamines. The quaternary ammonium compounds may be derived from triethanolamines. The alkanolamines from which the quaternary ammonium compounds are derived may be alkylated mono- or dialkanolamines, for example C1-C4 alkylated alkanolamines, preferably C1 alkylated alkanolamines (e.g, N-methyldiethanolamine).

The alkyl quaternary ammonium compounds may comprise a quaternized nitrogen atom that is substituted, at least in part. The quaternized nitrogen atom may be substituted, at least in part, with one or more C1-C3 alkyl or C1-C3 hydroxyl alkyl groups. The quaternized nitrogen atom may be substituted, at least in part, with a moiety selected from the group consisting of methyl, ethyl, propyl, hydroxyethyl, 2-hydroxypropyl, 1-methyl-2-hydroxyethyl, poly($C_2$-$C_3$ alkoxy), polyethoxy, benzyl, more preferably methyl or hydroxyethyl.

The alkyl quaternary ammonium compounds may comprise compounds of Formula (I):

$$\{R_{4\text{-}m}—N^+—[Z—Y—R^1]m\}X^- \quad (I)$$

where each R is independently selected from a hydrogen, a short chain $C_1$-$C_6$ group, such as a $C_1$-$C_3$ alkyl group or a $C_1$-$C_3$ hydroxyalkyl group (for example, each R may be a methyl group, an ethyl group, a propyl group, a hydroxyethyl group, or the like), a poly($C_{2-3}$ alkoxy) group, a polyethoxy group, or a benzyl group; each Z is independently selected from $(CH_2)_n$, $CH_2—CH(CH_3)—$ or $CH—(CH_3)—CH_2—$; each Y may comprise —O—(O)C—, —C(O)—O—, —NR—C(O)—, or —C(O)—NR—; each m is from 1, 2, or 3, preferably each m is 2 or 3; each n is from 1 to 4, preferably 2; the sum of carbon atoms in each $R^1$, plus one if Y is —O—(O)C— or —NR—C(O)—, may be twelve to twenty-two, or fourteen to twenty, with each $R^1$ being a hydrocarbyl or substituted hydrocarbyl group; and $X^-$ may comprise any compatible anion. X— may be independently selected from the group consisting of chloride, methyl sulfate, and ethyl sulfate, preferably $X^-$ is selected from the group consisting of chloride and methyl sulfate, more preferably X— is methyl sulfate. It may be preferred that Z is independently selected from $—CH_2—CH(CH_3)—$ and $—CH—(CH_3)—CH_2—$ to improve the hydrolytic stability of quaternary ammonium esters of Formula (I).

These types of agents and general methods of making them are disclosed in U.S. Pat. No. 4,137,180.

A second type of suitable quaternary ammonium compound has Formula (II):

$$[R_{4\text{-}m}—N^+—R^1{}_m]X^- \quad (II)$$

where each R, $R^1$, m and $X^-$ have the same meanings as disclosed above, with regard to Formula (I).

Suitable alkyl quaternary ammonium esters, according to Formula (I) or Formula (II) include materials selected from the group consisting of monoester quaternary material, diester quaternary material, triester quaternary material, and mixtures thereof. The level of monoester quat may be from 2.0% to 40.0% or from 15.0% to 35.0%, the level of diester quat may be from 40.0% to 98.0% or from 40.0% to 60.0%, and the level of triester quat may be from 0.0% to 30.0% or be from 10% to 38.0%, by weight of total ester quat. The relative amounts of mono-, di-, and triester quats may be determined by the method described in US Patent Publication No. 20220154106A1. An ester quat material may be produced in a two-step synthesis process. First, an esteramine may be produced by running an esterification reaction using fatty acids and an alkanolamine. In a second step, the product may be quaternized using an alkylating agent.

Examples of suitable quaternary ammonium compounds are commercially available from KAO Chemicals under the trade name Tetranyl® AT-1 and Tetranyl® AT-7590, from Evonik under the tradename Rewoquat® WE16 DPG, Rewoquat® WE18, Rewoquat® WE20, Rewoquat® WE28, and Rewoquat® 38 DPG, from Stepan under the tradename Stepantex® GA90, Stepantex® VR90, Stepantex® VK90, Stepantex® VA90, Stepantex® DC90, Stepantex® VL90A, Stepantex® SP90HV, Stepantex® VM85G, Stepantex® PA88E, Stepantex® PA85G, and Praepagen® TQN. Also, quaternary ammonium compounds and general methods of making them are disclosed in U.S. Pat. No. 4,137,180.

Linear Polymer

The menstrual fluid simulant compositions disclosed herein comprise linear polymers, where the term linear refers to polymers that are not crosslinked. The menstrual fluid simulant compositions may comprise from about 0.1% to about 5%, preferably from about 0.1% to about 4%, more preferably from about 0.1% to about 3% by weight of the simulant compositions of linear polymers. The menstrual fluid simulant compositions may comprise from about 0.1% to about 2% by weight of the simulant compositions of linear polymers. Nonionic high molecular weight (e.g., about 1,000 kDa to about 25,000 kDa) linear polymers are preferred. The linear polymers may have viscosity average molecular weights ($M_V$) greater than or equal to 2,000 kDa. The linear polymers may have viscosity average molecular weights ($M_V$) ranging from about 100 kDa to about 25,000 kDa, or from about 500 kDa to about 20,000 kDa, or from about 1,000 kDa to about 15,000 kDa, or from about 2,000 kDa to about 10,000 kDa. The linear polymer may be dissolved in a solvent and provided in the form of a solution. A solution of a nonionic linear polymer may contain a solvent comprising water and/or an organic solvent. Suitable nonionic linear polymers include polyacrylamides (PAAM) and polyethylene oxides (PEO). Suitable nonionic, linear, high molecular weight polymers include polyacrylamides (PAAM) and polyethylene oxides (PEO) having viscosity average molecular weights ($M_V$) greater than or equal to 2,000 kDa (e.g., 4,000 kDa PEO, 8,000 kDA PEO, 7,000 kDa PAAM).

Inorganic Salt

The menstrual fluid simulant compositions disclosed herein comprise inorganic salts. The menstrual fluid simulant compositions may comprise from about 0.05% to about 0.9% by weight of the simulant compositions of inorganic salts. Examples of suitable inorganic salts include sodium chloride (NaCl) and potassium chloride (KCl).

Dye

The menstrual fluid simulant compositions disclosed herein may comprise a dye, to give the menstrual fluid simulant a color that approximates the color of real menstrual fluid. The menstrual fluid simulant compositions may comprise from about 0.1% to about 2%, or about 0.1% to about 1%, by weight of the simulant compositions of a dye.

The compositions disclosed herein may comprise polymeric or non-polymeric dyes, organic or inorganic pigments, or mixtures thereof. A polymeric dye comprises a chromophore constituent and a polymeric constituent, where the polymeric constituent may be covalently bound to the chromophore constituent, directly or indirectly via a linking group. Examples of suitable polymeric constituents include polyoxyalkylene chains having multiple repeating units. Suitable polymeric dyes include the Liquitint® polymeric colorants available from Milliken Chemical (some of the exemplary menstrual fluid simulant described herein contain a combination of Milliken Liquitint® polymeric colorants (e.g., 53.8% Liquitint Red PR®, 32.5% Liquitint Yellow LP® and 13.7% Liquitint Aquamarine®). The pigments may be water-based pigments. Suitable water-based pigments include those designed for use in inkjet printers, for example, Hostajet® pigments made by Clariant. The pigments may have particle sizes of about 20 nm to about 150 nm. Pigments that have particle sizes within this range tend to remain in suspension. Red, magenta, yellow, and/or black pigments may be used in combination to mimic the visual appearance of menstrual fluid. In selecting the optimal dye, the visual appearance of the menstrual fluid simulant (to mimic the color of real menstrual fluid) and the ability of the dye(s) to remain in suspension (not settle) are considerations.

Water

The menstrual fluid simulant compositions disclosed herein comprise water (e.g., deionized water). The menstrual fluid simulant compositions may comprise from about 30% to about 97%, or about 30% to about 90%, or about 40% to about 80%, by weight of the simulant compositions of water.

Method of Making

The present disclosure relates to processes for making a menstrual fluid simulant composition as described herein. The process of making a menstrual fluid simulant composition may comprise the step of forming a vesicle dispersion of a quaternary ammonium compound, as describe herein, and combining the vesicle dispersion with a linear, nonionic polymer, an organic salt, a dye, and water (e.g., deionized water).

One or more of the materials, for example, the vesicle dispersion, may be formed in a batch process, in a circulation loop process, and/or by an in-line mixing process. Suitable equipment for use in the processes disclosed herein may include continuous stirred tank reactors, homogenizers, turbine agitators, recirculating pumps, paddle mixers, high shear mixers, static mixers, plough shear mixers, ribbon blenders, vertical axis granulators and drum mixers, both in batch and, where available, in continuous process configurations, spray dryers, and extruders.

The vesicle dispersions disclosed herein may be prepared by combining the components thereof in any convenient order and by mixing, e.g., agitating, the resulting component combination, preferably to form a phase stable composition. A fluid matrix may be formed containing at least a major proportion, or even substantially all, of the fluid components with the fluid components being thoroughly admixed by imparting shear agitation to this liquid combination. For example, rapid stirring with a mechanical stirrer may be employed. Additional non-limiting examples of processes for making vesicle dispersions are described in in US Pat. Pub. No. 2013/0109612, US Pat. Pub. No. 2018/0179470, U.S. Pat. No. 10,815,450, both of which are hereby incorporated herein by reference.

Use

The menstrual fluid simulant compositions disclosed herein may be used to assess or measure fluid distribution in absorbent articles, using any suitable analytical test method. Suitable analytical test methods are described in U.S. Pat. No. 11,020,289 (fluid distribution), U.S. Pat. No. 10,371,652 (fluid distribution), US Pat. Pub. No. 2022/0104973 (Stain Size Measurement Method, Repetitive Acquisition and Rewet Method), U.S. Pat. No. 11,291,595 (Run-off Test Method), and US Pat. Pub. No. 2022/0071814 (Moisture Absorption Capacity Test Method), all of which are hereby incorporated herein by reference.

COMBINATIONS

Specifically contemplated combinations of the disclosure are herein described in the following lettered paragraphs. These combinations are intended to be illustrative in nature and are not intended to be limiting.

A. A menstrual fluid simulant composition comprising:

a) from about 1 to about 60% by weight of the simulant composition of a vesicle dispersion of a quaternary ammonium compound of Formula (I) or Formula (II), preferably Formula (I):

$$\{R_{4-m}\text{—}N^{+}\text{—}[Z\text{—}Y\text{—}R^{1}]_{m}\}X^{-} \quad (I)$$

$$[R_{4-m}\text{—}N^{+}\text{—}R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—$CH(CH_3)$— or $CH$—$(CH_3)$—$CH_2$—; each Y comprises —O—(O)C—, —C(O)—O—, —NR—C(O)—, or —C(O)—

NR—; each m is 1, 2, or 3, preferably each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b) from about 0.1% to about 3% by weight of the simulant composition of a linear, nonionic polymer having a viscosity average molecular weight (MV) greater than or equal to 100 kDA and less than 25.000 kDA;

c) from about 0.05% to about 0.9% by weight of the simulant composition of an inorganic salt;

d) from about 0.1% to about 2% by weight of the simulant composition of a dye; and e) water, preferably deionized water;

where the menstrual fluid simulant composition has a viscosity that is shear-dependent and ranges from about 10 mPas to about 140 mPas, at 21° C. and at a shear rate of 10 $s^{-1}$.

B. A menstrual fluid simulant composition comprising:

a) from about 1 to about 60% by weight of the simulant composition of a vesicle dispersion of a quaternary ammonium compound of Formula (I) or Formula (II), preferably Formula (I):

$$\{R_{4\text{-}m}\text{—}N^+\text{—}[Z\text{—}Y\text{—}R^1]m\}X^- \quad \text{(I)}$$

$$[R_{4\text{-}m}\text{—}N^+\text{—}R^1{}_m]X^- \quad \text{(II)}$$

where each R is independently selected from a hydrogen, a short chain $C_1$-$C_6$ group, a poly($C_{2\text{-}3}$ alkoxy) group, a polyethoxy group, or a benzyl group; each Z is independently selected from $(CH_2)_n$, $CH_2$—$CH(CH_3)$— or CH—$(CH_3)$—$CH_2$—; each Y comprises —O—(O)C—, —C(O)—O—, —NR—C(O)—, or —C(O)—NR—; each m is 1, 2, or 3, preferably each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b) from about 0.1% to about 3% by weight of the simulant composition of a linear, nonionic polymer having a viscosity average molecular weight ($M_V$) greater than or equal to 100 kDA;

c) from about 0.05% to about 0.9% by weight of the simulant composition of an inorganic salt;

d) from about 0.1% to about 2% by weight of the simulant composition of a dye; and e) water, preferably deionized water;

where the menstrual fluid simulant composition has a filament breakup time of about 100 to about 3000 ms, preferably between about 200 ms and about 1500 ms, more preferably between about 300 ms and 800 ms, measured using the Capillary Breakup Extensional Rheometry (CaBER) described herein.

C. A menstrual fluid simulant composition comprising:

a) from about 1% to about 60% by weight of the simulant composition of a vesicle dispersion of a quaternary ammonium compound of Formula (I) or Formula (II), preferably Formula (I):

$$\{R_{4\text{-}m}\text{—}N^+\text{—}[Z\text{—}Y\text{—}R^1]m\}X^- \quad \text{(I)}$$

$$[R_{4\text{-}m}\text{—}N^+\text{—}R^1{}_m]X^- \quad \text{(II)}$$

where each R is independently selected from a hydrogen, a short chain $C_1$-$C_6$ group, a poly($C_{2\text{-}3}$ alkoxy) group, a polyethoxy group, or a benzyl group; each Z is independently selected from $(CH_2)_n$, $CH_2$—$CH(CH_3)$— or CH—$(CH_3)$—$CH_2$—; each Y comprises —O—(O)C—, —C(O)—O—, —NR—C(O)—, or —C(O)—NR—; each m is 1, 2, or 3, preferably each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate;

b) from about 0.1% to about 3% by weight of the simulant composition of a linear, nonionic polymer having a viscosity average molecular weights ($M_V$) greater than or equal to 100 kDA;

c) from about 0.05% to about 0.9% by weight of the simulant composition of an inorganic salt;

d) from about 0.1% to about 2% by weight of the simulant composition of a dye; and e) water, preferably deionized water;

where the menstrual fluid simulant composition has a surface tension that ranges from about 35 mN/m to about 70 mN/m.

D. A menstrual fluid simulant composition, where the menstrual fluid simulant composition has a filament breakup time of about 100 to about 3000 ms, preferably between about 200 ms and about 1500 ms, more preferably between about 300 ms and 800 ms, measured using the Capillary Breakup Extensional Rheometry (CaBER) described herein, a viscosity that is shear-dependent and ranges from about 10 mPas to about 140 mPas, at 21° C. and a shear rate of 10 s-1, a surface tension that ranges from about 35 mN/m to about 70 mN/m, or a combination thereof.

E. The menstrual fluid simulant composition according to any one of the preceding paragraphs, where the composition is non-animal-based.

F. The menstrual fluid simulant composition according to any one of the preceding paragraphs, where the viscosity of the menstrual fluid simulant composition decreases as shear rate increases.

G. The menstrual fluid simulant composition according to any one of the preceding paragraphs, where the vesicle dispersion has a mean particle size diameter ranging from about 1 μm to about 10 μm.

H. The menstrual fluid simulant composition according to any one of the preceding paragraphs, where the vesicle dispersion comprises from about 0.1% to about 10% by weight of the vesicle dispersion of the quaternary ammonium compound of Formula (I) or Formula (II).

I. The menstrual fluid simulant composition according to any one of the preceding paragraphs, where the vesicle dispersion comprises from about 0.001% to about 1% by weight of the vesicle dispersion of a pH-adjusting agent.

J. The menstrual fluid simulant composition according to any one of the preceding paragraphs, where the vesicle dispersion comprises from about 0.1% to about 3% by weight of the vesicle dispersion of a low molecular weight alcohol, preferably isopropanol.

K. A method of making a menstrual fluid simulant composition comprising the steps of:
  a. dissolving a dye and an inorganic salt in water, preferably deionized water, to form a first solution and mixing the first solution;
  b. adding a linear polymer having a molecular weight greater than or equal to 100 kDA to the first solution to form a second solution and mixing the second solution;
  c. adding and optionally mixing a quaternary ammonium compound of Formula (I) or Formula (II), preferably Formula (I), to the second solution to form the menstrual fluid simulant composition:

$$\{R_{4-m}—N^{+}—[Z—Y—R^{1}]m\}X^{-} \quad (I)$$

$$[R_{4-m}—N^{+}—R^{1}_{m}]X^{-} \quad (II)$$

where each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2$—$CH(CH_3)$— or CH—$(CH_3)$—$CH_2$—; each Y comprises —O—(O)C—, —C(O)—O—, —NR—C(O)—, or —C(O)—NR—; each m is 1, 2, or 3, preferably each m is 2 or 3; each n is from 1 to 4, preferably 2; the sum of carbon atoms in each $R^1$, plus one if Y is —O—(O)C— or —NR—C(O)—, is twelve to twenty-two, preferably fourteen to twenty, with each $R^1$ being a hydrocarbyl or substituted hydrocarbyl group; and $X^-$ is independently selected from the group consisting of chloride, methyl sulfate, and ethyl sulfate, preferably $X^-$ is selected from the group consisting of chloride and methyl sulfate, more preferably X— is methyl sulfate.

L. A method for assessing absorbent articles for their fluid handling ability, the method comprising the steps of:
  a. providing an absorbent article;
  b. loading the absorbent structure with the menstrual fluid simulant composition according to any one of the preceding paragraphs;
  c. visually assessing the loaded absorbent article for soiling.

M. The method of paragraph L, whereby the performance of the absorbent article is assessed by the shape, size, and/or location of the soiling.

N. A method for assessing absorbent articles, the method comprising the steps of:
  a. providing an absorbent article;
  b. loading the absorbent structure with the menstrual fluid simulant composition of according to any one of the preceding paragraphs;
  c. assessing the loaded absorbent article using a test method disclosed in the EDANA Guidelines for Testing Feminine Hygiene Products, Version 13 December 2018, as updated in August 2022.

TEST METHODS

Method for Measuring Viscosity

The viscosity of fluid to be tested is determined by performing a shear flow ramp on a rotational rheometer (e.g., DHR3, TA Instruments, New Castle, DE, USA). The rotational rheometer is operated in a cone and plate configuration using a stainless steel cone that is 60 mm in diameter, a cone (mounted as upper tooling) that has a 2° cone angle, and a temperature controllable Peltier plate (mounted as bottom tooling). The temperature of the Peltier plate is set to 21° C.+/−1° C.

The fluid to be tested is loaded on the rheometer peltier plate, the gap is set to 74 μm, any excess protruding sample is trimmed, and the gap is then set to 48 μm. The temperature is set to 21° C.+/−1° C. and the sample is equilibrated for 2 minutes. The shear stress is then recorded at eleven different shear rates logarithmically equidistant to one another and ranging from 1 $s^{-1}$ to 100 $s^{-}$, namely at shear rates of 1.00 $s^{-}$, 1.59 $s^{-}$, 2.51 $s^{-}$, 3.98 $s^{-}$, 6.31 $s^{-}$, 10 $s^{-}$, 15.85 $s^{-}$, 25.12 $s^{-}$, 39.81 $s^{-}$, 63.10 $s^{-}$, 100.00 $s^{-}$. The viscosity parameter is reported at a shear rate of 10 $s^{-1}$ in millipascal seconds (mPa·s) to the nearest hundred mPa·s. The same data may also be used to compute a shear thinning parameter or index. To compute the shear thinning index, the data are plotted in logarithmic scale, with shear rate on the abscissa and shear stress on the ordinate. A linear fit is then performed. Starting at the high-shear-rate end of the range, at least eight and as many consecutive points as possible are included, to achieve a linearity value R2 value of 0.9 or greater. If a linearity value $R^2$>0.9 cannot be achieved by fitting a linear regression to only eight points, the fit of the eight points corresponding to the highest shear rates is accepted as result. The value of the slope is defined as the shear thinning parameter, which is reported to the nearest 0.001.

Method for Measuring Capillary Breakup Extensional Rheometry

The breakup time of the fluid to be tested is determined using a Capillary Breakup Extensional Rheometer (CaBER). A sample of the fluid to be tested is loaded between two measurement plates and then exposed to a rapid extensional step strain by moving the upper plate upwards, thereby forming a fluid filament. The sample is loaded with a syringe, such as the Inkjet®-F syringe from B. Braun, 1 mL size syringe. Once the sample has been pulled into the syringe, precision tips are attached to the syringe. 0.05 mL (+/−0.01 mL) of sample is gently filled into the initial measurement gap. Care is taken to avoid air bubbles, as well as underfilling or overflowing of the sample, during loading of the sample. After loading the sample, the sample chamber is closed by pulling down the upper sliding door and the test is started after 60 seconds of equilibration time has passed. The sampling mode of the instrument is set to 1000 Hz for 2 seconds. The instrument continually measures the sample filament diameter over time until the filament brakes, after the upper plate has reached its final position.

The time evolution of the filament diameter during capillary thinning is controlled by a balance of capillary, viscous, and elastic forces. A laser micrometer measures the midpoint diameter of the gradually thinning fluid filament after the upper plate has reached its final position. An exemplary rheometer is the HAAKE CaBER 1 (Thermo Fisher Scientific, Karlsruhe, Germany), which is operated with the Haake CaBER Software V. 5.0.12.0. Stainless steel plates supplied by the manufacturer, which are 6 mm in diameter, are used as upper and lower measurement plates in the rheometer. These rheometer plates are mounted axially in the rheometer unit. The lower plate is mounted on a manual micrometer (an exemplary micrometer is the Holex Micrometer head, 0-25 mm range, 0.002 scale), which allows for vertical adjustment of the plate position.

Vertical adjustment of the plate position is used to define the geometry height for the experiment. The upper plate is mounted to a linear drive motor, which is capable of enabling a fast extensional strike with constant velocity within the range of 10-100 ms. Specifically, a linear stretch profile is used with an extensional deformation defined by constant velocity of the upper drive motor. The duration of the extensional deformation is set to 50 ms. The initial gap between the upper and lower plate is set at 1.5 mm. The micrometer screw, which is connected to the bottom plate, is used to adjust the height of the bottom plate to achieve an imposed step strain of 2.0. This imposed step strain is defined as the natural logarithm of the final sample height divided by the initial gap. The temperature of the rheometer is managed by a connected cooling thermostat, which is set it to 21° C. (+/−0.5° C.).

The breakup time, which is defined as the point when the filament diameter is equal to or less than 30 μm, of the real menses and the menstrual fluid simulant composition is reported in millisecond (ms) to the nearest millisecond.

Method for Measuring Surface Tension

The surface tension of the fluid to be tested is determined by method: ASTM D1331-20, following Method C—Surface Tension by Wilhelmy plate.

NMR MOUSE—Fluid Distribution Method

The NMR MOUSE fluid distribution method is described in U.S. Pat. No. 10,371,652, which is hereby incorporated herein by reference.

Other Test Methods

The menstrual fluid simulant compositions disclosed herein may be used in any acquisition, rewet, and/or other fluid handling test methods known in the art.

The present disclosure relates to a method for assessing absorbent articles, the method comprising the steps of: providing an absorbent article; loading the absorbent structure with a menstrual fluid simulant composition disclosed herein; and assessing the loaded absorbent article using a test method for assessing the fluid handling of the absorbent article, such as acquisition or rewet.

The present disclosure also relates to a method for assessing absorbent articles, the method comprising the steps of: providing an absorbent article; loading the absorbent structure with a menstrual fluid simulant composition disclosed herein; and assessing the loaded absorbent article using a test method disclosed in the EDANA Guidelines for Testing Feminine Hygiene Products, Version 13 December 2018, as updated in August 2022, which are hereby incorporated by reference.

The present disclosure also relates to a method for assessing absorbent articles for their fluid handling ability, the method comprising the steps of: providing an absorbent article; loading the absorbent structure with a menstrual fluid simulant composition disclosed herein; visually assessing the loaded absorbent article for soiling. The performance of the absorbent article may be assessed by the shape, size, and/or location of the soiling.

EXAMPLES

The examples provided below are intended to be illustrative in nature and are not intended to be limiting.

Preparation of menstrual fluid simulant compositions 1-6: Menstrual fluid simulant compositions 1-6 are prepared by the process steps described below, creating a total fluid volume of 300 ml for each composition. First, the specified concentrations shown in Table 1 of polymeric dye, sodium chloride, and deionized water are poured into a 600 ml glass beaker that has an inner diameter of 10 cm. This mixture is then stirred at 500 rpm for two minutes at 23+/−2° C., to ensure uniform mixing, using a polymeric paddle with a diameter of 5 cm, where the position of the paddle is 0.5 cm above the bottom of the glass beaker. The specified concentration of polyethylene oxide (PEO) is then slowly (e.g., 5 mg every 2 seconds) added, while mixing at 500 rpm, to the mixture of polymeric dye, sodium chloride, and distilled water, in order to prevent agglomeration of the polyethylene oxide. After the total concentration of polyethylene oxide is added to the mixture of polymeric dye, sodium chloride, and deionized water, the mixture of polymeric dye, sodium salt, polyethylene oxide, and deionized water is stirred at 500 rpm for 20 minutes at room temperature to fully dissolve the PEO. Afterwards, the specified concentration of the specified vesicle dispersion is then slowly added to the mixture of polymeric dye, sodium salt, polyethylene oxide, and deionized water, while mixing the mixture at 500 rpm to create a final total volume of 300 ml. The mixture of polymeric dye, sodium salt, polyethylene oxide, vesicle dispersion, and deionized water is then stirred for 20 minutes at 500 rpm. The resulting menstrual fluid simulant composition is stored inside a sealed glass bottle at 23+/−2° C. for 12 hours in the dark before use, for example, before any viscosity or breakup time measurements are taken. For the NMR MOUSE fluid distribution method, a contrast agent, specifically 0.1 Mol/L solution of $MnCl_2$ solution, is added to a menstrual fluid simulant composition and the mixture of menstrual fluid simulant composition and contrast agent is mixed via shaking for 30 minutes, at room temperature, at 150 rpm, just before testing. The prepared fluids are stored in the dark at 23+/−2° C. in a sealed glass bottle.

Preparation of Paper Industrial Fluid (PIF). PIF has the following components: 950 ml deionized water, 10 g NaCl, 15 g Sodium Carboxymethyl Cellulose (CMC) (CAS 9004-32-4, low viscosity, Sigma Aldrich C5678), 80 g Glycerin, 4 g Sodium Bicarbonate (NaHCO3). To prepare PIF, the water is added to a glass beaker at room temperature. Heat the solution up to 45° C. and stir at 500 rpm. Afterwards add the CMC slowly in small portions by using a spatula during stirring at 500 rpm. After the total CMC has been added, the solution is stirred at 500 rpm for half an hour and continues to be heated at 45° C. until the total CMC has been dissolved. Heating is stopped when the CMC is completely dissolved. The solution is then cooled down to 23+/−2° C. and stirred at 500 rpm. The glycerin, the NaCl and the sodium bicarbonate are added and the solution is stirred at 500 rpm for 1 hour.

Example I—Measured Viscosities and Breakup Times

The viscosities and breakup times of menstrual fluid simulant example compositions 1-6 are measured over time, starting when the compositions are made and up to 40 days of storage, under controlled lab conditions (23±2° C. and 50±10% relative humidity) in closed glass bottles. The glass bottles are stored in darkness (e.g., a dark cupboard). The viscosities and breakup times are measured according to the test methods described above. The shear thinning indices of menstrual fluid simulant example compositions 1-6 are also calculated, according to the method described above.

Figure 2:
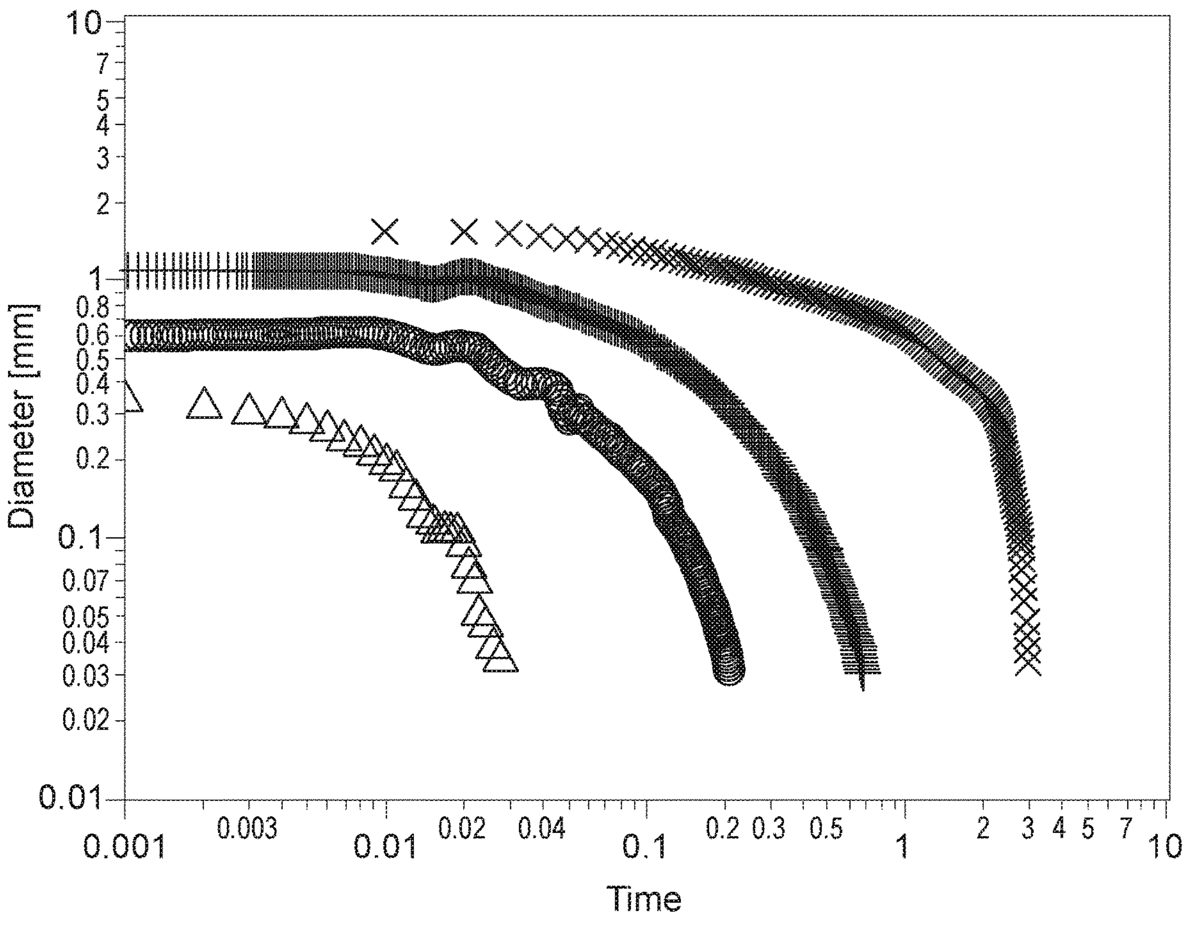
FIG. 2 is a graphic representation of filament diameter as a function of time and shows the breakup time—the point in time when the filament diameter is equal to or less than 30 μm—of the menstrual fluid simulant example compositions 1 and 2 and two samples (high and low) of real menses.

Further, the viscosities of real menstrual fluid from one panelist (menses A) is measured and breakup times of real menstrual fluid from another panelist (menses B) is measured. Several menstrual fluid samples are collected from both panelists during the first two days of their menstrual cycles using menstrual cups. The samples are then transferred into medicine plastic vials and stored in a refrigerator overnight. The viscosity and breakup time of each sample is measured within 24 hours of sampling and the highest and lowest viscosities (menses A) and breakup times (menses B) are reported. The shear thinning indices corresponding to the highest and lowest viscosities (menses A) are also calculated, according to the method described above.

from 28 ms to 2963 ms, indicating the high variability of the rheological properties of menses. With reference to the graph in FIG. 1, this graph shows the lowest and highest viscosity values observed for menses from panelist A, as well as the viscosities of menstrual fluid simulant example compositions 1 and 2 and PIF, all measured at a range of shear rates. With reference to the graph in FIG. 2, this graph shows the lowest and highest breakup times observed for menses from panelist B, as well as the breakup times observed for the menstrual fluid simulant example compositions 1 and 2. Together, FIGS. 1 and 2 show that the rheological behavior of PIF is different than the rheological behavior of both menses and the menstrual fluid simulant example compositions 1 and 2. PIF shows Newtonian behavior with constant viscosity over the measured shear rate range. In contrast, the menstrual fluid simulant example compositions 1 and 2 show shear thinning behavior that is similar to that of menses. The breakup times of the menstrual fluid simulant example compositions 1 and 2 are also within the range of breakup times observed for menses. Notably, for PIF, no filament is formed and, therefore, a breakup time cannot be measured.

TABLE 1

| Ingredients (% by weight) | Real Menses | PIF | Ex. 1 | Ex. 2 | Ex. 3 | Ex. 4 | Ex. 5 | Ex. 6 |
|---|---|---|---|---|---|---|---|---|
| Deionized Water | N/A | N/A | 49.83 | 49.67 | 49.61 | 49.86 | 49.41 | 49.45 |
| Vesicle Dispersion 1 (Mean PSD µ2 m, 7% active) | N/A | N/A | 49.84 | 49.66 | 49.61 | 0 | 0 | 0 |
| Vesicle Dispersion 2 (Mean PSD 6.2 µm, 6% active) | N/A | N/A | 0 | 0 | 0 | 49.82 | 0 | 49.31 |
| Vesicle Dispersion 3 (Mean PSD 6.2 µm, 4% active) | N/A | N/A | 0 | 0 | 0 | 0 | 49.32 | 0 |
| PEO (4000 kDa) | N/A | N/A | 0.25 | 0.60 | 0.25 | 0.25 | 0.25 | 0 |
| PEO (8000 kDa) | N/A | N/A | 0 | 0 | 0 | 0 | 0 | 0.21 |
| NaCl | N/A | N/A | 0.05 | 0.05 | 0.50 | 0.05 | 0.05 | 0.05 |
| Polymeric Dye[1] | N/A | N/A | 0.98 | 0.98 | 0.98 | 0.98 | 0.98 | 0.98 |
| Viscosity at shear rate of $10\ s^{-1}$ (mPas) | 24.9-70 (panelist A) | 11.5 | 26.3 | 123.5 | 38.2 | 28.3 | 21.7 | 50.2 |
| Shear Thinning Index | 0.705-0.554 | 0.989 | 0.732 | 0.588 | 0.676 | 0.751 | 0.788 | 0.599 |
| Viscosity Stability (days) | N/A | <15 | ≥40 | ≥40 | ≥40 | ≥40 | Not measured | Not measured |
| Breakup Time (ms) | 28-2963 (panelist B) | no filament* | 236 | 677 | 213 | 312 | 277 | 952 |
| Breakup-Time Stability (days) | N/A | N/A | ≥40 | ≥40 | ≥25 | ≥40 | N/A | N/A |

[1] The polymeric dye contains 53.8% Liquitint Red PR ®, 32.5% Liquitint Yellow LP ® and 13.7% Liquitint Aquamarine ®.

*PIF does not form a filament, therefore breakup time cannot be measured.

TABLE 2

| Ingredients (% by weight) | Vesicle Dispersion 1 | Vesicle Dispersion 2 | Vesicle Dispersion 3 |
|---|---|---|---|
| NaHEDP Chelant | 0.0072 | 0.007 | 0 |
| Formic Acid | 0.045 | 0.045 | 0.053 |
| Hydrochloric acid | 0.0074 | 0.0075 | 0.0234 |
| DEEDMAC [2] | 7.0 | 5.0 | 4.0 |
| Isopropanol | 0.7 | 0.5 | 0.4 |
| Silicone antifoam [3] | 0.081 | 0.0 | 0.02 |
| Deionized water | Balance | Balance | Balance |
| Mean PSD[4] | 2 µm | 6.2 µm | 6.2 µm |

[1] Vesicle dispersions 1,2, and 3 are made according to the process described in US Patent Publication No. 2018/0179470, pages 9-10).

[2] Reaction product of Methyl-diethanolamine with fatty acids, in molar ratio ranging from 1:1.5 to 1:2, quaternized with methylchloride. The fatty acid has a chain length distribution of 35-55% saturated C18 chains, 10-25% mono-unsaturated C18 chains, and has an iodine value of 20.

[3] Xiameter AFE-2010, supplied by Dow, 8% silicone content.

[4] Measured according to the Method for Measuring Particle Size Distribution of a Vesicle Dispersion, which is described above.

The data in Table 1 show that the viscosity of real menstrual fluid from a single panelist (panelist A) can vary from 24.9 mPa·s to 70 mPa·s and the breakup-time of real menstrual fluid from a single panelist (panelist B) can vary The data in Table 1 also show that the viscosities of menstrual fluid simulant example compositions 1, 2, 3 and 4, at 40 days of storage under the conditions described above, do not change, where "not changing" means that the viscosity value changes less than 20% versus the viscosity value measured 48 hours after making the menstrual fluid simulant composition. The data in Table 1 also show that the breakup times of menstrual fluid simulant example compositions 1, 2, and 4, at 40 days of storage under the conditions described above, do not change, where "not changing" means that the breakup time changes less than 20% versus the breakup time measured 48 hours after making the menstrual fluid simulant composition. For menstrual fluid simulant example composition 3, the breakup time at 25 days of storage under the conditions described above, does not change, where "not changing" means that the breakup time changes less than 20% versus the breakup time measured 48 hours after making the menstrual fluid simulant composition.

Example II. Fluid Distribution in Feminine Hygiene Product

Figure 3:
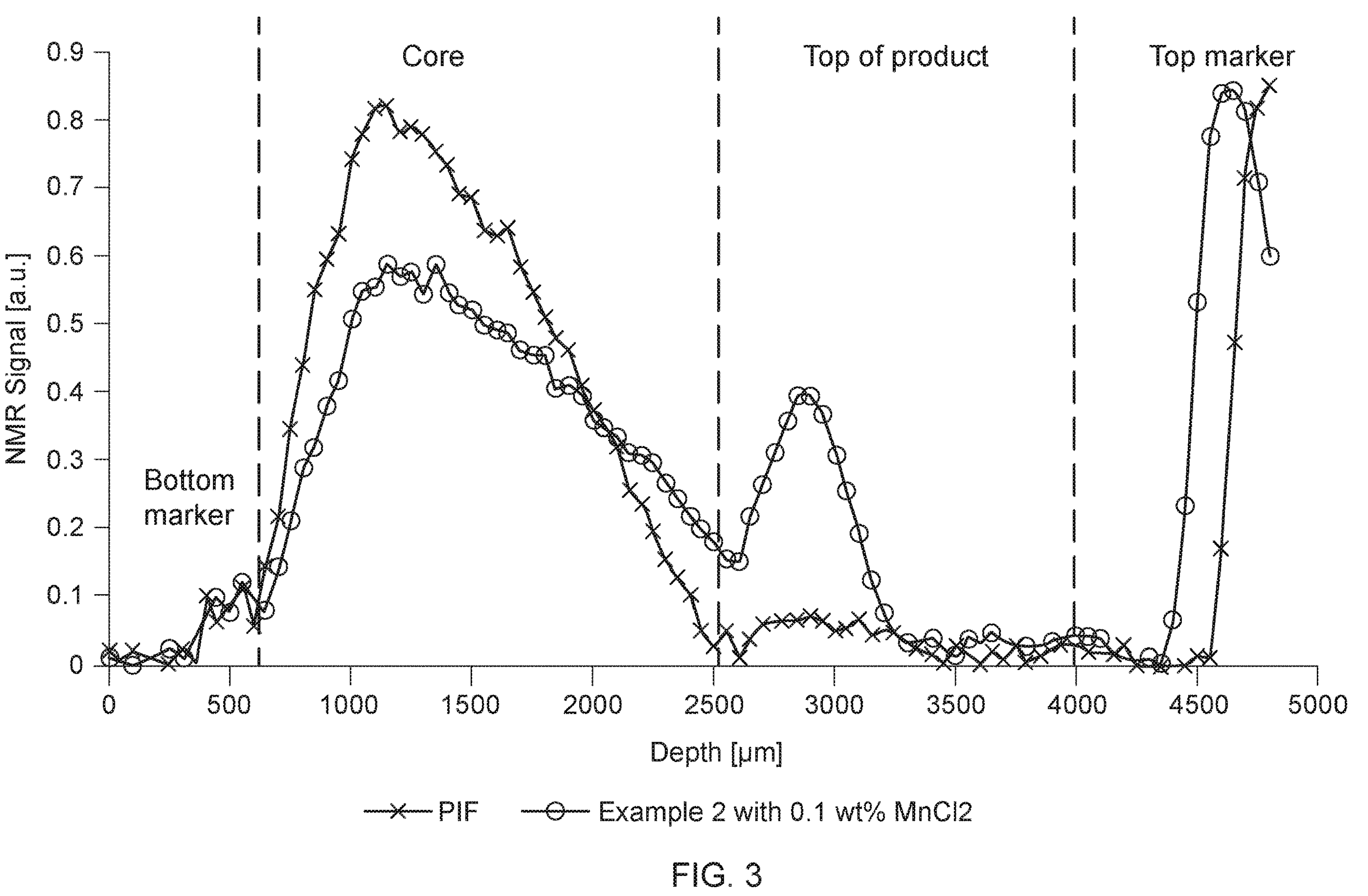
FIG. 3 is a graphic representation of the distributions of the menstrual fluid simulant example composition 2 and Paper Industrial Fluid (PIF), within an Always Ultra Pad.

Breakup time is a proxy for stringiness, which affects the interaction and distribution of a fluid with and in a hygiene product, as shown in the NMR measurements graphed in FIG. 3.

The graph of FIG. 3 (and data in Table 3) show the fluid distribution of PIF and the fluid distribution of menstrual fluid simulant example composition 2, in the same feminine hygiene product. As shown in FIG. 3 (and Table 3), the fluid distribution of PIF is very different from the fluid distribution of menstrual fluid simulant example composition 2, due to the Non-Newtonian behavior of real menses versus the Newtonian behavior of PIF. For example, the graph of FIG. 3 (and Table 3) shows that the total volume of fluid inside the core is 953 µl of 1000 µl for PIF versus 782 µl of 1000 µl for menstrual fluid simulant example composition 2. Furthermore, it can be inferred from the graph of FIG. 3 (and Table 3), that breakup time and stringiness, as well as viscosity, affect fluid distribution in a feminine hygiene product. More specifically, the use of PIF in fluid distribution testing may overestimate the performance of the tested feminine hygiene product, because, unlike real menses, PIF does not exhibit stringiness (no breakup time), does not exhibit shear thinning behavior, and also contains no particles.

TABLE 3

Liquid Distribution Quantification for Always Ultra Pad Product

| Test liquid | Liquid Volume in Top of Product [2500 µm to 4000 µm] (µL) | Liquid Volume in Product Core [700 µm to 2500 µm] (µL) |
|---|---|---|
| PIF | 47 | 953 |
| Ex. 2 with 0.1% wt $MnCl_2$ | 218 | 782 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A menstrual fluid simulant composition comprising:

a. from 1 to 60% by weight of the simulant composition of a vesicle dispersion of a quaternary ammonium compound of Formula (I) or Formula (II):

$$\{R_{4-m}—N^+—[Z—Y—R^1]_m\}X^- \quad (I)$$

$$[R_{4-m}—N^+—R^1{}_m]X^- \quad (II)$$

wherein each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2—CH(CH_3)—$ or $CH—(CH_3)—CH_2—$; each Y comprises —O—(O)C—, —C(O)—O—, —NR—C(O)—, or —C(O)—NR—; each m is 2 or 3; each n is from 1 to 4; the sum of carbon atoms in each $R^1$, plus one if Y is —O—(O)C— or —NR—C(O)—, is twelve to twenty-two, with each $R^1$ being a hydrocarbyl or substituted hydrocarbyl group; and $X^-$ is independently selected from the group consisting of chloride, methyl sulfate, and ethyl sulfate;

b. from 0.1% to 3% by weight of the simulant composition of a linear, nonionic polymer selected from the group consisting of polyacrylamides and polyethylene oxides, the linear, nonionic polymer having a viscosity average molecular weight ($M_V$) greater than or equal to 100 kDA and less than 25,000 kDA;

c. from 0.05% to 0.9% by weight of the simulant composition of an inorganic salt;

d. from 0.1% to 2% by weight of the simulant composition of a dye; and e. water;

wherein the menstrual fluid simulant composition has a viscosity that is shear-dependent and ranges from 10 mPas to 140 mPas, at 21° C. and a shear rate of 10 s-1.

2. The menstrual fluid simulant composition according to claim 1, wherein the composition comprises from 1 to 60% by weight of the simulant composition of a vesicle dispersion of a quaternary ammonium compound of Formula (I):

$$\{R_{4-m}—N^+—[Z—Y—R^1]_m\}X^- \quad (I)$$

wherein each R is independently selected from a hydrogen, a short chain $C_1$-$C_6$ group, a poly($C_{2-3}$ alkoxy) group, a polyethoxy group, or a benzyl group; each Z is independently selected from $(CH_2)_n$, $CH_2—CH(CH_3)—$ or $CH—(CH_3)—CH_2—$; each Y comprises —O—(O)C—, —C(O)—O—, —NR—C(O)—, or —C(O)—NR—; each m is 2 or 3; each n is 2; the sum of carbon atoms in each $R^1$, plus one if Y is —O—(O)C— or —NR—C(O)—, is fourteen to twenty, with each $R^1$ being a hydrocarbyl or substituted hydrocarbyl group; and $X^-$ is independently selected from the group consisting of chloride and methyl sulfate.

3. The menstrual fluid simulant composition according to claim 2, wherein X— is methyl sulfate.

4. The menstrual fluid simulant composition according to claim 1, wherein the composition is non-animal-based.

5. The menstrual fluid simulant composition according to claim 1, wherein the viscosity of the menstrual fluid simulant composition decreases as shear rate increases.

6. The menstrual fluid simulant composition according to claim 1, wherein the vesicle dispersion has a mean particle size diameter ranging from 1 μm to 10 μm.

7. The menstrual fluid simulant composition according to claim 1, wherein the vesicle dispersion comprises from 0.1% to 10% by weight of the vesicle dispersion of the quaternary ammonium compound of Formula (I) or Formula (II).

8. The menstrual fluid simulant composition according to claim 1, wherein the vesicle dispersion comprises from 0.001% to 1% by weight of the vesicle dispersion of a pH-adjusting agent.

9. The menstrual fluid simulant composition according to claim 1, wherein the vesicle dispersion comprises from 0.1% to 3% by weight of the vesicle dispersion of isopropanol.

10. The menstrual fluid simulant composition according to claim 1, wherein the vesicle dispersion has a pH from 2.0 to 6.0.

11. The menstrual fluid simulant composition according to claim 1, wherein the linear, nonionic polymer has a viscosity average molecular weight (MV) greater than or equal to 2,000 kDa.

12. The menstrual fluid simulant composition according to claim 1, wherein the quaternary ammonium compound is derived from a fatty acid feedstock having an iodine value of 1 to 60.

13. The menstrual fluid simulant composition according to claim 1, wherein the dye comprises a water-based pigment having a particle size of 20 nm to 150 nm.

14. A method for assessing absorbent articles for their fluid handling ability, the method comprising the steps of:

a. providing an absorbent article;

b. loading the absorbent structure with the menstrual fluid simulant composition according to claim 1;

c. visually assessing the loaded absorbent article for soiling.

15. The method of claim 14, whereby the performance of the absorbent article is assessed by the shape, size, and/or location of the soiling.

16. A method for assessing absorbent articles, the method comprising the steps of:

a. providing an absorbent article;

b. loading the absorbent structure with the menstrual fluid simulant composition according to claim 1;

c. assessing the loaded absorbent article using a test method disclosed in the EDANA Guidelines for Testing Feminine Hygiene Products, Version 13 December 2018, as updated in August 2022.

17. A menstrual fluid simulant composition comprising:

a. from 1 to 60% by weight of the simulant composition of a vesicle dispersion of a quaternary ammonium compound of Formula (I) or Formula (II):

$$\{R_{4\text{-}m}—N^+—[Z—Y—R^1]_m\}X^- \quad (I)$$

$$[R_{4\text{-}m}—N^+—R^1{}_m]X^- \quad (II)$$

wherein each R is independently selected from a hydrogen, a short chain $C_1$-$C_6$ group, a poly($C_{2\text{-}3}$ alkoxy) group, a polyethoxy group, or a benzyl group; each Z is independently selected from $(CH_2)_n$, $CH_2$—CH ($CH_3$)— or CH—($CH_3$)—$CH_2$—; each Y comprises —O—(O)C—, —C(O)—O—, —NR—C(O)—, or —C(O)—NR—; each m is 2 or 3; each n is from 1 to 4; the sum of carbon atoms in each $R^1$, plus one if Y is —O—(O)C— or —NR—C(O)—, is twelve to twenty-two, with each $R^1$ being a hydrocarbyl or substituted hydrocarbyl group; and $X^-$ is independently selected from the group consisting of chloride, methyl sulfate, and ethyl sulfate;

b. from 0.1% to 3% by weight of the simulant composition of a linear, nonionic polymer selected from the group consisting of polyacrylamides and polyethylene oxides, the linear, nonionic polymer having a viscosity average molecular weight ($M_V$) greater than or equal to 100 kDA;

c. from 0.05% to 0.9% by weight of the simulant composition of an inorganic salt;

d. from 0.1% to 2% by weight of the simulant composition of a dye; and e. water;

wherein the menstrual fluid simulant composition has a filament breakup time of 100 to 3000 ms, measured using the Capillary Breakup Extensional Rheometry (CaBER) described herein.

18. The menstrual fluid simulant composition according to claim 17, wherein the menstrual fluid simulant composition has a filament breakup time between 200 ms and 1500 ms, measured using the Capillary Breakup Extensional Rheometry (CaBER) described herein.

19. The menstrual fluid simulant composition according to claim 18, wherein the menstrual fluid simulant composition has a filament breakup time between 300 ms and 800 ms, measured using the Capillary Breakup Extensional Rheometry (CaBER) described herein.

20. A menstrual fluid simulant composition comprising:

a. from 1% to 60% by weight of the simulant composition of a vesicle dispersion of a quaternary ammonium compound of Formula (I) or Formula (II):

$$\{R_{4\text{-}m}—N^+—[Z—Y—R^1]_m\}X^- \quad (I)$$

$$[R_{4\text{-}m}—N^+—R^1{}_m]X^- \quad (II)$$

wherein each R is independently selected from a hydrogen, a short chain $C_1$-$C_6$ group, a poly($C_{2\text{-}3}$ alkoxy) group, a polyethoxy group, or a benzyl group; each Z is independently selected from $(CH_2)_n$, $CH_2$—CH ($CH_3$)— or CH—($CH_3$)—$CH_2$—; each Y comprises —O—(O)C—, —C(O)—O—, —NR—C(O)—, or —C(O)—NR—; each m is 2 or 3; each n is from 1 to 4; the sum of carbon atoms in each $R^1$, plus one if Y is —O—(O)C— or —NR—C(O)—, is twelve to twenty-two, with each $R^1$ being a hydrocarbyl or substituted hydrocarbyl group; and $X^-$ is independently selected from the group consisting of chloride, methyl sulfate, and ethyl sulfate;

b. from 0.1% to 3% by weight of the simulant composition of a linear, nonionic polymer selected from the group consisting of polyacrylamides and polyethylene oxides, the linear, nonionic polymer having a viscosity average molecular weights ($M_V$) greater than or equal to 100 kDA;

c. from 0.05% to 0.9% by weight of the simulant composition of an inorganic salt;

d. from 0.1% to 2% by weight of the simulant composition of a dye; and e. water;

wherein the menstrual fluid simulant composition has a surface tension that ranges from 35 mN/m to 70 mN/m.

* * * * *